United States Patent [19]

Berg

[11] Patent Number: 5,879,517
[45] Date of Patent: Mar. 9, 1999

[54] METHOD FOR SEPARATING 2-BUTANOL FROM T-AMYL ALCOHOL USING CERTAIN ORGANIC COMPOUNDS AS THE AGENT IN EXTRACTIVE DISTILLATION

[76] Inventor: Lloyd Berg, 1314 S. 3rd Ave., Bozeman, Mont. 59715

[21] Appl. No.: 93,641

[22] Filed: Jun. 9, 1998

[51] Int. Cl.⁶ .............................. B01D 3/40; C07C 29/84
[52] U.S. Cl. ................................ 203/57; 203/58; 203/59; 203/60; 203/62; 203/63; 203/65; 203/67; 203/69; 203/70; 568/913
[58] Field of Search .................................. 203/57, 60, 59, 203/62, 67, 69, 68, 70, 63, 58, 65; 568/913

[56] References Cited

U.S. PATENT DOCUMENTS

| | | |
|---|---|---|
| 3,989,601 | 11/1976 | Boozalis et al. ........................... 203/63 |
| 4,693,788 | 9/1987 | Berg ........................................... 203/57 |
| 4,756,803 | 7/1988 | Berg ........................................... 203/60 |
| 4,935,103 | 6/1990 | Berg et al. ................................. 203/65 |
| 4,969,977 | 11/1990 | Berg ........................................... 203/65 |
| 5,207,876 | 5/1993 | Berg et al. ............................... 568/913 |
| 5,360,520 | 11/1994 | Berg ......................................... 568/913 |
| 5,504,239 | 4/1996 | Mehl et al. .............................. 568/913 |
| 5,759,359 | 6/1998 | Berg ........................................... 203/57 |

*Primary Examiner*—Virginia Manoharan

[57] ABSTRACT

2-Butanol cannot be sparated from t-amyl alcohol by distillation or rectification because of the closeness of their boiling points. 2-Butanol is readily separated from t-amyl alcohol by extractive distillation. Effective agents are butyl ether, benzyl acetate and 1,2,4-trimethyl benzene.

1 Claim, No Drawings

METHOD FOR SEPARATING 2-BUTANOL FROM T-AMYL ALCOHOL USING CERTAIN ORGANIC COMPOUNDS AS THE AGENT IN EXTRACTIVE DISTILLATION

FIELD OF THE INVENTION

This invention relates to a method for separating 2-butanol from t-amyl alcohol using certain organic compounds as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the highest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

TABLE 1

Effect of Relative Volatility on Theoretical stage Requirements.

| Separation Purity, | Relative Volatility | | | | | | | |
|---|---|---|---|---|---|---|---|---|
| Both Products (Mole Fraction) | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

2-Butanol and t-amyl alcohol boil two degrees apart and have a relative volatility of 1.22 which makes it difficult to separate them by conventional distillation or rectification. Table 2 shows that with an agent giving a relative volatility of 1.6, only twenty-seven actual plates are required to get 99% purity compared to 61 plates for straight rectification.

TABLE 2

Theoretical and Actual Plates Required vs. Relative Volatility for 2-Butanol from Isobutanol Separation

| Relative Volatility | Theoretical Plates Required At Total Reflux, 99% Purity | Actual Plates Required, 75% Efficiency |
|---|---|---|
| 1.4 | 26 | 35 |
| 1.5 | 22 | 30 |
| 1.6 | 20 | 27 |

OBJECTIVE OF THE INVENTION

The object of this invention is to provide a process or method of extractive distillation that will enhance the relative volatility of 2-butanol and L-amyl alcohol in their separation in a rectification column. It is a further object of this invention to identify effective extractive distillation agents that are stable and can be recycled.

SUMMARY OF THE INVENTION

The objects of this invention are provided by a process for the separation of 2-butanol and t-amyl alcohol which entails the use of certain organic compounds when employed as the agent in extractive distillation.

DETAILED DESCRIPTION OF THE INVENTION

I have discovered that certain organic compounds will effectively increase the relative volatility between 2-butanol and t-amyl alcohol during rectification when employed as the agent in extractive distillation. They are benzyl acetate, ethyl benzoate, 2-(2-butoxyethoxy)ethyl acetate, 2-octanone, isobutyl acetate, isobutyl butyrate, ethyl salicylate, ethyl nonanate, o-xylene, cumene, n-nonane, decalin, 1-decene, dodecane, cymene, myrcene, diethyl benzene, butyl ether, beta-pinene, dipropyl amine, 4-methyl morpholine, 2-nitrotoluene, benzonitrile, 3-ethyl phenol, ethyl benzene, 1,2,4-trimethyl benzene and 3-carene.

THE USEFULNESS OF THE INVENTION

The usefulness of this invention can be demonstrated by referring to the data presented in Tables 1, 2 and 3. All of the successful agents show that 2-butanol can be separated from t-amyl alcohol by means of extractive distillation in a rectification column and that the ease or separation as measured by relative volatility is considerable.

WORKING EXAMPLE

1. Fifty grams of 2-butanol—t-amyl alcohol mixture and fifty grams of butyl ether were charged to a vapor-liquid equilibrium still and refluxed for two hours. The vapor composition was 75.2%. 2-butanol and 24.8% t-amyl alcohol; the liquid composition was 68.2% 2-butanol and 31.8% t-amyl alcohol. This is a relative volatility of 1.4.

TABLE 3

Effective Extractive Distillation Agents For
Separating 2-Butanol From tert. Amyl Alcohol

| Compounds | Relative Volatility |
|---|---|
| None | 1.2 |
| Benzyl acetate | 1.5 |
| 2-(2-Butoxyethoxy)ethyl acetate | 1.35 |
| Ethyl benzoate | 1.4 |
| 2-Octanone | 1.4 |
| Isobutyl acetate | 1.5 |
| Isobutyl butyrate | 1.4 |
| Ethyl salicylate | 1.3 |
| Ethyl nonanate | 1.3 |
| o-Xylene | 1.3 |
| Cumene | 1.3 |
| n-Nonane | 1.3 |
| Decalin | 1.4 |
| 1-Decene | 1.3 |
| Dodecane | 1.3 |
| Cymene | 1.3 |
| beta-Pinene | 1.3 |
| Myrcene | 1.3 |
| Diethyl benzene | 1.3 |
| Butyl ether | 1.4 |
| Dipropyl amine | 1.3 |
| 4-Methyl morpholine | 1.3 |
| 2-Nitrotoluene | 1.4 |
| Benzonitrile | 1.3 |
| 3-Ethyl phenol | 1.6 |
| Ethyl benzene | 1.3 |
| 1,2,4-Trimethyl benzene | 1.4 |
| 3-Carene | 1.3 |

I claim:

1. A method for recovering 2-butanol from a mixture of 2-butanol and t-amyl alcohol which comprises distilling a mixture of 2-butanol and t-amyl alcohol in the presence of an extractive distillation agent, recovering the 2-butanol as overhead product and obtaining the t-amyl alcohol and the extractive distillation agent as bottoms product, wherein said extractive distillation agent consists of one material selected from the group consisting of benzyl acetate, ethyl benzoate, isobutyl acetate, 2-octanone, 2-(2-butoxyethy)ethyl acetate, isobutyl butyrate, ethyl salicylate, ethyl nonanate, o-xylene, cumene, n-nonane, decalin, 1-decene, dodecane, cymene, beta-pinene, myrcene, diethyl benzene, butyl ether, dipropyl amine, 4-methyl morpholine, 2-nitrotoluene, benzonitrile, 3-ethyl phenol, ethyl benzene, 1,2,4-trimethylbenzene and 3-carene.

* * * * *